United States Patent
Rosenberry et al.

(10) Patent No.: US 10,656,368 B1
(45) Date of Patent: May 19, 2020

(54) METHOD AND SYSTEM FOR BIOLOGICAL IMAGING USING A WIDE FIELD OBJECTIVE LENS

(71) Applicant: Omniome, Inc., San Diego, CA (US)

(72) Inventors: Donald V. Rosenberry, San Diego, CA (US); Dale Buermann, San Diego, CA (US)

(73) Assignee: OMNIOME, INC., San Diego, CA (US)

( * ) Notice: Subject to any disclaimer, the term of this patent is extended or adjusted under 35 U.S.C. 154(b) by 0 days.

(21) Appl. No.: 16/521,464

(22) Filed: Jul. 24, 2019

(51) Int. Cl.
G02B 21/00 (2006.01)
G02B 7/02 (2006.01)
C12Q 1/6869 (2018.01)
G02B 3/00 (2006.01)
G02B 21/02 (2006.01)
G01N 21/90 (2006.01)
G01N 21/64 (2006.01)

(52) U.S. Cl.
CPC ........... *G02B 7/021* (2013.01); *C12Q 1/6869* (2013.01); *G02B 3/0037* (2013.01); *G02B 21/02* (2013.01); *G01N 21/6458* (2013.01); *G01N 21/9072* (2013.01)

(58) Field of Classification Search
CPC .... G02B 21/02; G02B 21/33; G02B 27/0068; G02B 3/00; G02B 21/22; G02B 13/22; G02B 13/24; G02B 7/021; G02B 13/003; G02B 13/04; G02B 9/04; G02B 9/10; G02B 13/006; G02B 21/16; G02B 21/025
See application file for complete search history.

(56) References Cited

U.S. PATENT DOCUMENTS

| | | |
|---|---|---|
| 3,481,665 A | 12/1969 | Rosenberger |
| 3,915,558 A | 10/1975 | Glatzel |
| 4,025,170 A | 5/1977 | Kawamura |
| 4,124,798 A | 11/1978 | Thompson |
| 5,130,238 A | 7/1992 | Malek et al. |
| 5,455,166 A | 10/1995 | Walker |
| 5,508,846 A | 4/1996 | Hall |
| 5,599,675 A | 2/1997 | Brenner et al. |
| 5,625,495 A | 4/1997 | Moskovich |
| 5,641,658 A | 6/1997 | Adams et al. |
| 5,695,934 A | 12/1997 | Brenner |
| 5,750,341 A | 5/1998 | Macevicz |

(Continued)

FOREIGN PATENT DOCUMENTS

| | | |
|---|---|---|
| EP | 2166398 | 3/2010 |
| WO | 89/10977 | 11/1989 |

(Continued)

OTHER PUBLICATIONS

U.S. Appl. No. 62/807,934.

(Continued)

*Primary Examiner* — Alicia M Harrington
(74) *Attorney, Agent, or Firm* — Kilpatrick Townsend & Stockton LLP

(57) ABSTRACT

An objective lens is used for DNA sequencing. An example system includes a flow cell, the objective lens, and a camera. Light from the flow cell is imaged by the camera through the objective lens. The objective lens can provide a long working distance; a flat field curvature; a high numerical aperture; and/or a wide field of view.

20 Claims, 4 Drawing Sheets

(56) References Cited

U.S. PATENT DOCUMENTS

| | | |
|---|---|---|
| 5,805,359 A | 9/1998 | Yamanashi |
| 5,863,722 A | 1/1999 | Brenner |
| 5,888,737 A | 3/1999 | DuBridge et al. |
| 6,140,489 A | 10/2000 | Brenner |
| 6,175,002 B1 | 1/2001 | Dubridge et al. |
| 6,201,642 B1 | 3/2001 | Bos |
| 6,210,891 B1 | 4/2001 | Nyren et al. |
| 6,214,587 B1 | 4/2001 | Dattagupta et al. |
| 6,258,568 B1 | 7/2001 | Nyren |
| 6,266,459 B1 | 7/2001 | Walt et al. |
| 6,274,320 B1 | 8/2001 | Rothberg et al. |
| 6,355,431 B1 | 3/2002 | Chee et al. |
| 6,366,398 B1 * | 4/2002 | Ouchi .................. G02B 21/248 359/368 |
| 6,388,819 B1 | 5/2002 | Leidig |
| 6,770,441 B2 | 8/2004 | Dickinson et al. |
| 6,859,570 B2 | 2/2005 | Walt et al. |
| 7,057,026 B2 | 6/2006 | Barnes et al. |
| 7,115,400 B1 | 10/2006 | Adessi et al. |
| 7,211,414 B2 | 5/2007 | Hardin et al. |
| 7,315,019 B2 | 1/2008 | Turner et al. |
| 7,329,492 B2 | 2/2008 | Hardin et al. |
| 7,329,860 B2 | 2/2008 | Feng et al. |
| 7,405,281 B2 | 7/2008 | Xu et al. |
| 7,622,294 B2 | 11/2009 | Walt et al. |
| 7,929,211 B2 | 4/2011 | Chuang |
| 7,929,221 B2 | 4/2011 | Ning |
| 8,778,848 B2 * | 7/2014 | Lin ..................... G01N 27/447 422/68.1 |
| 8,951,781 B2 | 2/2015 | Williamson et al. |
| 9,045,796 B2 | 6/2015 | Gunderson et al. |
| 9,193,996 B2 | 11/2015 | Buermann et al. |
| 9,476,080 B2 | 10/2016 | Li et al. |
| 10,161,003 B2 | 12/2018 | Stromberg et al. |
| 2002/0055100 A1 | 5/2002 | Kawashima et al. |
| 2004/0002090 A1 | 1/2004 | Mayer et al. |
| 2004/0096853 A1 | 5/2004 | Mayer |
| 2005/0064460 A1 | 3/2005 | Holliger et al. |
| 2005/0130173 A1 | 6/2005 | Leamon et al. |
| 2006/0077563 A1 | 4/2006 | Mihara et al. |
| 2006/0187556 A1 | 8/2006 | Inoko |
| 2007/0007991 A1 | 1/2007 | Lee et al. |
| 2007/0099208 A1 | 5/2007 | Drmanac et al. |
| 2007/0128624 A1 | 6/2007 | Gormley et al. |
| 2008/0009420 A1 | 1/2008 | Schroth et al. |
| 2008/0108082 A1 | 5/2008 | Rank et al. |
| 2008/0117527 A1 | 5/2008 | Nuno et al. |
| 2009/0026082 A1 | 1/2009 | Rothberg et al. |
| 2009/0127589 A1 | 5/2009 | Rothberg et al. |
| 2009/0247414 A1 | 10/2009 | Obradovic et al. |
| 2010/0111768 A1 | 5/2010 | Banerjee et al. |
| 2010/0137143 A1 | 6/2010 | Rothberg et al. |
| 2010/0282617 A1 | 11/2010 | Rothberg et al. |
| 2012/0270305 A1 | 10/2012 | Reed et al. |
| 2015/0103413 A1 | 4/2015 | Uchida et al. |
| 2015/0234149 A1 | 8/2015 | Kreitzer et al. |
| 2016/0091705 A1 | 3/2016 | Ben Ezra et al. |
| 2017/0022553 A1 | 1/2017 | Vijayan et al. |
| 2017/0168281 A1 * | 6/2017 | Furuya .................. G02B 21/02 |
| 2018/0044727 A1 | 2/2018 | Vijayan et al. |
| 2018/0081149 A1 | 3/2018 | Bae et al. |
| 2018/0187245 A1 | 7/2018 | Dambacher et al. |
| 2018/0208983 A1 | 7/2018 | Dambacher et al. |
| 2018/0231750 A1 | 8/2018 | Byler |
| 2018/0259768 A1 * | 9/2018 | Watson .............. G02B 27/0025 |
| 2018/0280975 A1 | 10/2018 | Kilcoin et al. |
| 2019/0055598 A1 | 2/2019 | Buermann et al. |

FOREIGN PATENT DOCUMENTS

| | | |
|---|---|---|
| WO | 91/06678 | 5/1991 |
| WO | 00/63437 | 10/2000 |
| WO | 04/018497 | 3/2004 |
| WO | 05/010145 | 2/2005 |
| WO | 05/065814 | 7/2005 |
| WO | 2007123744 | 11/2007 |
| WO | 2010018727 | 2/2010 |
| WO | 2014074202 | 5/2014 |
| WO | 2018076330 | 5/2018 |

OTHER PUBLICATIONS

U.S. Appl. No. 62/859,886.

Bains, "A Novel Method for Nucleic Acid Sequencing", J. Theor. Biol., vol. 135, 1988, pp. 303-307.

Bentley et al., "Accurate Whole Human Genome Sequencing Using Reversible Terminator Chemistry", Nature, vol. 456, No. 7218, Nov. 6, 2008, pp. 53-59.

Dean et al., "Comprehensive Human Genome Amplification Using Multiple Displacement Amplification", Proc Natl Acad Sci USA, vol. 99, No. 8, Apr. 16, 2002, pp. 5261-5266.

Dressman et al., "Transforming Single DNA Molecules into Fluorescent Magnetic Particles for Detection and Enumeration of Genetic Variations", Proceedings of the National Academy of Sciences of the United States of America, vol. 100, No. 15, Jul. 22, 2003, pp. 8817-8822.

Drmanac et al., "Accurate Sequencing by Hybridization for DNA Diagnostic and Individual Genomics", Nature Biotechnology, Jan. 1998, 16, 54-58.

Fodor et al., "Light-Directed, Spatially Addressable Parallel Chemical Synthesis", Science vol. 251, Feb. 15, 1991, pp. 767-773.

Lage et al., "Whole Genome Analysis of Genetic Alterations in Small DNA Samples Using Hyperbranched Strand Displacement Amplification and Array-CGH", Genome Res., vol. 13, No. 2, Feb. 2003, pp. 294-307.

Lizardi et al., "Mutation Detection and Single-Molecule Counting Using Isothermal Rolling-Circle Amplification", Nature Genetics, vol. 19, No. 3, Jul. 1998, pp. 225-232.

Ronaghi et al., "DNA Sequencing: A Sequencing Method Based on Real-Time Pyrophosphate", Science, vol. 281, Issue 2375, Jul. 17, 1998, pp. 363-365.

Ronaghi, "Pyrosequencing sheds light on DNA sequencing.", Genome Res., vol. 11, No. 1, 2001, pp. 3-11.

Ronaghi et al., "Real-time DNA Sequencing using Detection of Pyrophosphate Release", Anal. Biochem., vol. 242, Dec. 1996, pp. 84-89.

Sambrook et al., "Molecular Cloning: A Laboratory Manual", Cold Spring Harbor, vol. 1, 3rd Edition, 2001, 79 pages.

Shendure et al., "Accurate Multiplex Polony Sequencing of an Evolved Bacterial Genome", Science, vol. 309, No. 5741, Sep. 9, 2005, pp. 1728-1732.

Walker et al., "Strand Displacement Amplification—An Isothermal, In Vitro DNA Amplification Technique", Nucleic Acids Res, vol. 20, No. 7, 1992, pp. 1691-1696.

\* cited by examiner

METHOD AND SYSTEM FOR BIOLOGICAL IMAGING USING A WIDE FIELD OBJECTIVE LENS

BACKGROUND OF THE INVENTION

The determination of nucleic acid sequence information is important in biological and medical research. The process of determining sequence information is commonly called "sequencing." The sequence information is helpful for identifying gene associations with diseases and phenotypes, identifying potential drug targets, and understanding the mechanisms of disease development and progress. Sequence information is an important part of personalized medicine, where it can be used to optimize diagnosis, treatment, or prevention of disease in a specific subject.

Given the wide applicability and utility of nucleic acid sequence information, improved systems and methods for sequencing are desired, for example to reduce the cost of obtaining sequence information.

SUMMARY OF THE INVENTION

Embodiments of the invention provide systems and methods for microscopic detection of analytes. In particular configurations, nucleic acids are detected in a sequencing system. According to one aspect, a system includes a flow cell, an objective lens, and a camera. Light from the flow cell is imaged by the camera through the objective lens. Among other benefits, the objective lens described herein can provide a long working distance; a flat field curvature; a high numerical aperture; and/or a wide field of view.

In some embodiments, a system for DNA sequencing comprises: a solid support configured for attachment of one or more analytes or reagents; an objective lens having a depth of field equal to or less than 1.5 microns; a camera configured to image luminescence from analytes or reagents on the solid support using the objective lens; a tube lens between the objective lens and the camera, the tube lens configured to focus light from the objective lens onto a sensor of the camera; an excitation source; and/or a dichroic mirror between the objective lens and the lens tube, the dichroic mirror configured to reflect light from the excitation source into the objective lens toward the solid support, wherein: light from the excitation source is configured to cause material of the analytes or reagents in the array to fluoresce, and/or, the dichroic mirror is at an angle less than 40 degrees with respect to the aspheric lens. The objective lens can comprise: a first doublet lens having a first lens and a second lens, wherein: the first lens of the first doublet lens has a concave and a convex surface, and the second lens of the first doublet lens has a concave and a convex surface; a second doublet lens having a first lens and a second lens, wherein: the first lens of the second doublet lens has a concave and a convex surface, and the second lens of the second doublet lens has a concave and a convex surface; a third doublet lens having a first lens and a second lens, wherein: the first lens of the third doublet lens has two convex surfaces, the second lens of the third doublet lens has two concave surfaces, and the second doublet lens is between the first doublet lens and the third doublet lens; a fourth doublet lens having a first lens and a second lens, wherein: the first lens of the fourth doublet lens has two concave surfaces, the second lens of the fourth doublet lens has two convex surfaces, the third doublet lens is between the second doublet lens and the fourth doublet lens, the first doublet lens is a first lens of an optical train of the objective lens and the fourth doublet lens is a last lens of the optical train of the objective lens, the first doublet lens is configured to be closer to the solid support than the fourth doublet lens, and/or optical rays are not infinity corrected after passing from the first doublet lens through the fourth doublet lens; a first singlet lens between the second doublet lens and the third doublet lens, the first singlet lens having two convex surfaces; a second singlet lens between the second doublet lens and the third doublet lens, the second singlet lens having two convex surfaces; an aspheric lens between the third doublet lens and the fourth doublet lens, wherein the aspheric lens has a diameter equal to or greater than 40 millimeters and equal to or less than 60 millimeters; and/or an aperture stop between the third doublet lens and the fourth doublet lens, wherein: the aperture stop is a physical aperture stop having one or more walls forming an opening, the aperture stop is within 25 millimeters of the aspheric lens, and/or the aperture stop is located at a distance between 70% and 90% in the optical train measured from the first doublet lens. In some embodiments, the objective lens has no more than 22 surfaces of lenses that affect optical power of the objective lens, 16 surfaces from four doublet lenses, four surfaces from two singlet lenses, and two surfaces from the aspheric lens; optical elements of the objective lens consist of four doublet lenses, two singlet lenses, the aspheric lens, and the aperture stop; and/or the solid support is part of a flow cell, the flow cell comprises a cover slip, and the cover slip is 1 millimeter thick.

In some embodiments, an apparatus for an objective lens of a microscope for imaging an array of nucleic acids comprises a plurality of lenses having simple surfaces, wherein: the plurality of lenses form an optical train, the optical train extending from a first lens to a last lens, and the plurality of lenses comprise four doublet lenses and no triplet lenses; an aperture stop, wherein: the aperture stop is a physical aperture stop, and the aperture stop is located between the first lens and the last lens; and/or an aspheric lens between the first lens and the last lens, the aspheric lens positioned within 25 millimeters of the aperture stop. In some embodiments, the first lens is configured to be closer to a specimen than the last lens; the aperture stop is located at a distance between 70% and 90% in the optical train as measured from the first lens; optical rays are not infinity corrected after passing through the last lens of the optical train; the aspheric lens has a diameter equal to or greater than 40 millimeters and equal to or less than 60 millimeters; the apparatus has a depth of field equal to or less than 1.5 microns; the apparatus has a numerical aperture between 0.6 and 0.8; and/or the apparatus has a field of view that is at least 1 mm$^2$.

In some embodiments, a system for DNA sequencing comprises: a solid support configured for attachment of an array of nucleic acids; an objective lens comprising: a plurality of lenses having simple surfaces, an aperture stop, wherein the aperture stop is a physical aperture stop, and an aspheric lens positioned within 25 millimeters of the aperture stop; and/or a camera configured to image the array using the objective lens. In some embodiments, the solid support is part of a flow cell, and the flow cell has a coverslip having a thickness equal to or greater than 0.3 millimeters and equal to or less than 2.0 millimeters; a first lens of the objective lens is separated by a distance from the solid support, and the distance is equal to or less than 10 millimeters and equal to or greater than 3 millimeters; the plurality of lenses form an optical train, the optical train extending from a first lens to a last lens; the plurality of lenses comprise four doublet lenses and no triplet lenses; the system has a depth of field equal to or less than 1.5 microns; the system has a numerical aperture between 0.6 and 0.8; the system has a field of view that is at least 4 mm²; and/or the system further comprises a mirror between the objective lens and the camera, wherein the mirror is at an angle less than 40 degrees with respect to the aspheric lens.

In some embodiments, a method for nucleic acid sequencing comprises: passing material through a flow cell, the material comprising a reagent for nucleic acid sequencing; illuminating the flow cell with light; imaging light from the flow cell through an objective lens using a camera sensor; wherein the objective lens comprises: a plurality of lenses having simple surfaces, an aperture stop, wherein the aperture stop is a physical aperture stop, and/or an aspheric lens positioned within 25 millimeters of the aperture stop.

BRIEF DESCRIPTION OF THE DRAWINGS

The present disclosure is described in conjunction with the appended figures.

In the appended figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION OF THE INVENTION

The ensuing description provides preferred exemplary embodiment(s), and is not intended to limit the scope, applicability, or configuration of the disclosure. Rather, the ensuing description of the preferred exemplary embodiment(s) will provide those skilled in the art with an enabling description for implementing a variety of exemplary embodiment. It is understood that various changes may be made in the function and arrangement of elements without departing from the spirit and scope as set forth in the appended claims.

The present disclosure sets forth, inter alia, embodiments that relate generally to optical systems, and more specifically, and without limitation, to an objective lens for a microscope.

Figure 1:
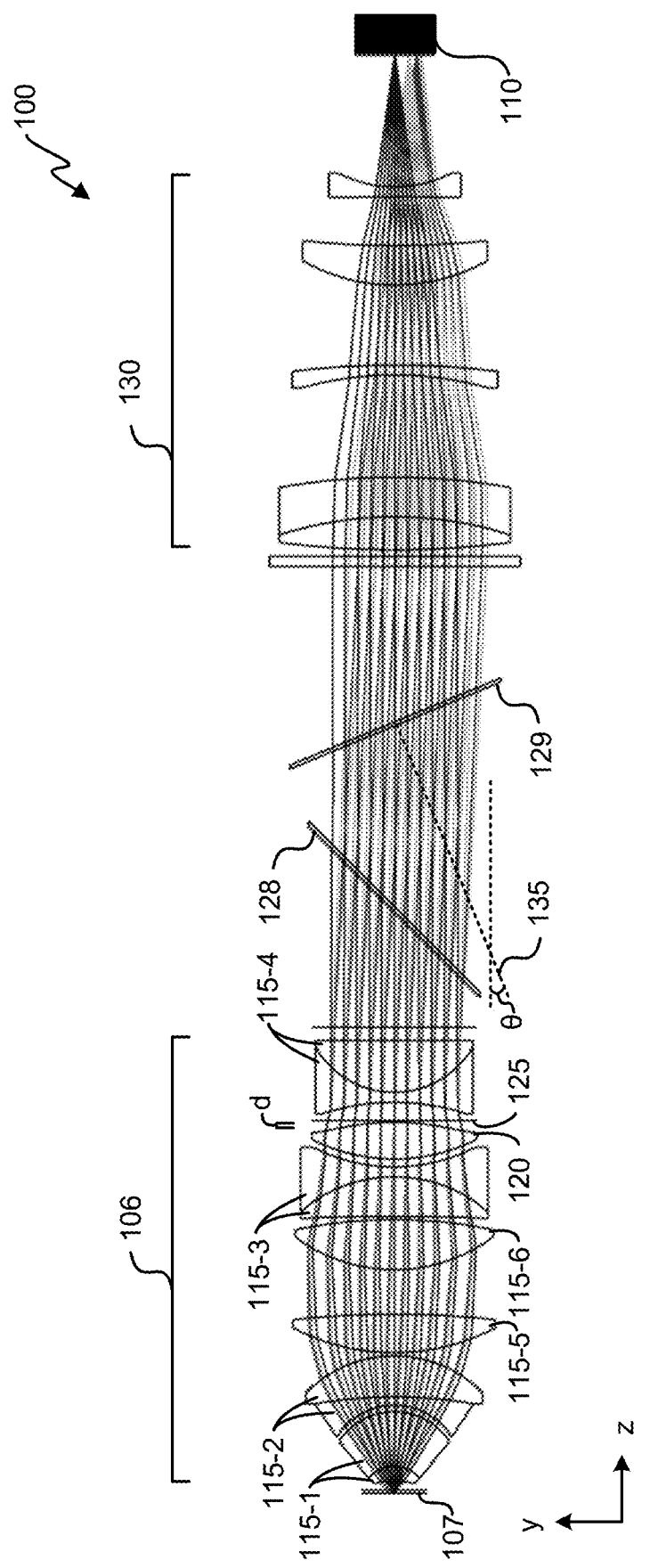
FIG. 1 shows a diagrammatic representation of an optical system for imaging a flow cell for DNA sequencing according to an embodiment of the present invention.

Referring first to FIG. 1, a diagrammatic representation of an embodiment of an optical system 100 for imaging a sample vessel, such as a flow cell for DNA sequencing, according to an embodiment of the present invention is shown. The optical system 100 includes an objective 106, a flow cell 107, and a sensor 110. Light from the flow cell 107 passes through the objective 106 before being imaged by the sensor 110.

The objective 106 comprises a plurality of lenses 115, an aspheric lens 120, and an aperture stop 125. The plurality of lenses 115 have simple surfaces. A simple surface is a surface that can be defined as a portion of a sphere or a cylinder, with a plane being a special case of a portion of a sphere having an infinite radius. The plurality of lenses 115 comprise a first lens 115-1, a second lens 115-2, a third lens 115-3, and a fourth lens 115-4. The plurality of lenses 115 form an optical train of the objective 106, with the optical train extending from the first lens 115-1 to a last lens (e.g., the fourth lens 115-4). The first lens 115-1, the second lens 115-2, the third lens 115-3, and the fourth lens 115-4 are doublet lenses, each doublet lens having two simple lenses joined together (e.g., by an epoxy). The first lens 115-1 is closer to the flow cell 107 (e.g., containing a specimen for imaging) than the last lens.

The plurality of lenses in the exemplary configuration of FIG. 1 includes a fifth lens 115-5 and a sixth lens 115-6 (between the second lens 115-2 and the third lens 115-3). The fifth lens 115-5 and the sixth lens 115-6 are simple lenses. In some embodiments, the fifth lens 115-5 is referred to as a first singlet lens and the sixth lens 115-6 is referred to as a second singlet lens. The plurality of lenses 115 exemplified in FIG. 1 does not include a triplet lens. A triplet lens has three simple lenses (e.g., bonded together with an epoxy). The fifth and sixth lenses have spherical surfaces. Aspheric lenses can be used instead but may be more costly.

The aperture stop 125 is a physical aperture stop. The aperture stop 125 has a wall (e.g., one wall for a circular aperture) or a plurality of walls forming an opening in the aperture stop 125. The aperture stop 125 is positioned between the first lens 115-1 and the last lens. The aspheric lens 120 is positioned a distance d away from the aperture stop 125 and is closer to the first lens 115-1 than the aperture stop 125. In some embodiments, the distance d is equal to or less than 30, 25, 20, 15, 10, 5, 3, 2, 1.5, or 1 millimeters (e.g., 1, 2, 3, or 11 millimeters).

The aperture stop 125 is located at a distance between 70% and 90% in the optical train of the objective 106, wherein zero is at a surface of the first lens 115-1 closest to the flow cell 107 and 100% is at a last surface of the last lens of the optical train of the objective 106. The aspheric lens 120 has a diameter equal to or greater than 40 millimeters and equal to or less than 60 millimeters (e.g., 40, 42, 45, 47, 50, 52, 55, 57, or 60 millimeters). In some embodiments, the large diameter of the aspheric lens 120 contributes to providing an objective 106 having a long working distance, a flat field curvature, a high numerical aperture, and/or a wide field of view. Although aspheric lens 120 plays a substantial role, the overall combination of lenses in objective 106 contributes to these characteristics.

An objective (e.g., objective 106) that is present in a system or method of the present disclosure can have a numerical aperture (NA) equal to or greater than 0.1 and equal to or less than 0.9. For example, NA can be between 0.5 and 0.9, between 0.6 and 0.9, between 0.7 and 0.9, between 0.5 and 0.8, or between 0.6 and 0.8. An objective or other transmitter can be configured to operate with a detection system that resolves features (e.g. nucleic acid sites) on a surface that are separated by less than 100 microns, 50 microns, 10 microns, 5 microns, 1 micron, or 0.5 micron. The detection system, including objective or other transmitter, can be configured to resolve features having an average area that is smaller than about 1 mm², 500 $\mu m^2$, 100 $\mu m^2$, 25 $\mu m^2$, 10 $\mu m^2$, 5 $\mu m^2$, 1 $\mu m^2$, 500 $nm^2$, or 100 $nm^2$.

An optical system set forth herein can have a field of view that is equal to or greater than 0.1 mm², 0.5 mm², 1 mm², 2 mm², 4 mm², 8 mm², 12 mm², 16 mm², 18 mm². Alternatively or additionally, the field of view can be configured to be equal to or less than 18 mm², 16 mm², 12 mm², 8 mm², 4 mm², 2 mm², 1 mm², 0.5 mm², 0.1 mm². A larger field of view can enable faster scanning of the flow cell 107.

An optical system of the present disclosure, such as the optical system 100, can have a depth of field equal to or less than 2.0, 1.75, 1.5, 1.25, 1.0, or 0.8 microns. Alternatively or additionally, the depth of field can be equal to or greater than 0.3, 0.4, 0.7, 1.0, 1.5 or 2.0 microns.

Rotationally symmetric polynomial aspheric surfaces can be described by a polynomial expansion of a deviation from a spherical (or aspheric described by a conic) surface. An even asphere surface model uses only even powers of a radial coordinate to describe asphericity. The even asphere surface model uses a base radius of curvature and a conic constant. Sag of an aspheric surface can be given by:

$$z(r) = \frac{cr^2}{1+\sqrt{1-(1+k)c^2r^2}} + \alpha_1 r^2 + \alpha_2 r^4 + \alpha_3 r^6 + \alpha_4 r^8 + \alpha_5 r^{10},$$

where $c=1/R$, R is the base radius of curvature, and k is the conic constant.

In some embodiments:

$\alpha_2 = 0 +/- 1, 3, 5\%$ $\alpha_4 = 2.13e\text{-}06 +/- 1, 3, 5\%$, e.g., $2.126e\text{-}06$, $2.148e\text{-}06$ $\alpha_6 = 1.0\ e\text{-}09 +/- 1, 3, 5\%$, e.g., $0.9967e\text{-}09$, $1.021e\text{-}09$ $\alpha_8 = 1.17e\text{-}12 +/- 1, 3, 5\%$, e.g., $1.146e\text{-}12$, $1.196e\text{-}12$ $\alpha_{10} = 1.1e\text{-}16 +/- 5, 10, 20\%$, e.g., $0.9054e\text{-}16$, $1.287e\text{-}16$ $R = 128$ mm $+/- 1, 3, 5\%$ $k = 0 +/- 1, 3, 5\%$ The above aspheric surface equation goes to a $10^{th}$ order. An equation can user higher order terms. It will be understood that a variety of models or equations that are known in the art pertaining to optics can be used instead of, or in combination with, the models and equations exemplified above.

Table I provides sample dimensions of the objective 106.

TABLE I

Sample Objective 106 Dimensions

| Element | Radius (+/- 1, 3, or 5%) (mm) | Thickness (+/- 1, 3, or 5%) (mm) | Diameter (+/- 5, 10, or 15%) (mm) |
|---|---|---|---|
| 115-1, 1st lens | -23.2<br>-35.7 | 2.61 | 17.46 |
| 115-1, 2nd lens | -35.7<br>-22.9 | 17.08 | 37.26 |
| Gap | | 1.54 | |
| 115-2, 1st lens | -30.8<br>443 | 2.52 | 37.66 |
| 115-2, 2nd lens | 439.4<br>-104 | 13.02 | 53.18 |
| Gap | | 0.95 | |
| 115-5 | 89.12 | 16.05 | 65.26 |

TABLE I-continued

Sample Objective 106 Dimensions

| Element | Radius (+/- 1, 3, or 5%) (mm) | Thickness (+/- 1, 3, or 5%) (mm) | Diameter (+/- 5, 10, or 15%) (mm) |
|---|---|---|---|
| | -96.3 | | |
| Gap | | 0.97 | |
| 115-6 | 60.65<br>-145 | 18 | 66.93 |
| Gap | | 0.93 | |
| 115-3, 1st lens | 95.97<br>-45.4 | 16.45 | 58.95 |
| 115-3, 2nd lens | -45.8<br>48.08 | 3.62 | 55.97 |
| Gap | | 3.32 | |
| 120 | 76.97<br>-128 | 10.06 | 52.31 |
| Gap | | 1.01 | |
| 125 | INF | | 41.24 |
| Gap | | 6.5 | |
| 115-4, 1st lens | -53.8<br>33.46 | 2.62 | 48.19 |
| 115-4, 2nd lens | 33.69<br>-75.6 | 17.97 | 51.26 |

Table II provides example values of the objective 106.

TABLE II

Example Values of Objective 106

| Element | Radius (mm) | Thickness (mm) | Diameter (mm) |
|---|---|---|---|
| 115-1, 1st lens | -23.01, -23.11, -23.20<br>-35.48, -35.53, -35.71, | 2.60, 2.61, 2.62 | 16.40, 17.19, 17.46 |
| 115-1, 2nd lens | -35.49, -35.72, -35.79<br>-22.80, -22.86, -22.90 | 17.00, 17.05, 1708 | 34, 35, 35.11 |
| Gap | | 1.526, 1.530, 1.540 | |
| 115-2, 1st lens | -30.73, -30.80, -30.89<br>437.54, 438.66, 443 | 2.50, 2.51, 2.52 | 36, 37.66, 38.91 |
| 115-2, 2nd lens | 438.65, 439.4, 441<br>-103.4, -103.7, -104 | 13, 13.02, 13.04 | 50, 50.84, 53.18 |
| Gap | | 0.945, 0.946, 0.95 | |
| 115-5 | 88.51, 88.76, 89.12<br>-95.36, -95.75, -96.3 | 15.87, 16, 16.05 | 59, 60, 62, 63.3, 66.9 |
| Gap | | 0.95, 0.96, 0.97 | |
| 115-6 | 60, 60.18, 60.39, 60.65<br>-112.21, -114.05, -145 | 17.76, 18, 18.13 | 59, 60, 62, 63.3, 66.9 |
| Gap | | 0.92, 0.97, 0.99 | |
| 115-3, 1st lens | 95.49, 95.97, 96.22<br>-44.84, -45.39, -45.4 | 16.05, 16.4, 16.45 | 52, 53, 54, 55 |
| 115-3, 2nd lens | -44.69, -45.4, -45.43<br>47.6, 47.7, 47.8 | 3.6, 3.63, 3.65 | 52, 53, 54, 55 |
| Gap | | 3.29, 3.3, 3.31 | |
| 120 | 75.91, 76.38, 76.55<br>-126.95, -127.45, -128.22 | 9.5, 10, 10.09, 11 | 45, 46, 48, 50 |
| Gap | | 0.8, 0.9, 1 | |
| 125 | INF | | 40, 45, 50 |
| Gap | | 6.49, 6.5, 6.53 | |
| 115-4, 1st lens | -53.3, -53.37, -53.45<br>33.25, 33.27, 33.43 | 2.4, 2.5, 2.6 | 41, 42, 43, 44, 45 |
| 115-4, 2nd lens | 33.26, 33.42, 33.57<br>-74.5, -74.85, -75.2 | 17.9, 17.94, 17.95 | 45, 46, 48, 50 |

The optical system 100 further comprises a focus dichroic mirror 128, an excitation dichroic mirror 129, and a tube lens 130. The focus dichroic mirror 128 is configured to couple light along an optical axis of the objective 106 for an autofocus system. The excitation dichroic mirror 129 is configured to couple light along the optical axis of the objective 106 to irradiate the flow cell 107 with excitation light provided by an excitation source (not shown). A sample in the flow cell 107 absorbs the excitation light and emits light by fluorescence. Light produced from the fluorescence travels through the objective 106 and toward the sensor 110.

In some embodiments, optical rays traveling from the flow cell 107 and through the objective 106 are not infinity corrected after passing through the objective 106. Generally, the light is collimated by the objective such that rays exiting the objective are collimated with respect to a point source. Nevertheless, as the rays pass through individual components of the objective the rays will locally converge, diverge or be collimated as exemplified by the ray trace in FIG. 1. Thus, as illustrated in FIG. 1, optical rays exiting the objective 106 in a direction toward the sensor 110, are not collimated but converging as light propagates to the tube lens 130. In some embodiments, light is diverging after exiting the objective 106. The tube lens 130 focuses light from the objective 106 to the sensor 110. The focus dichroic mirror 128 and the excitation dichroic mirror 129 are disposed between the objective 106 and the tube lens 130.

In some embodiments, the optical system 100 is used for nucleic acid sequencing. The flow cell 107 can contain an array of nucleic acids on a surface. Fluidic reagents used for sequencing can be flowed into and out of the flow cell. The objective 106 can be configured to observe the surface such the nucleic acids that are modified by the reagents can be detected. The objective 106 comprises a plurality of lenses 115 having simple surface, an aperture stop 125, an aspheric lens 120 positioned within 25 millimeters of the aperture stop 125, and/or a camera (e.g., sensor 110) configured to image content in the flow cell using the objective 106. In some embodiments, the objective 106 is referred to as an objective lens. The optical system 100 can include one or more beam splitters (e.g., focus dichroic mirror 128; excitation dichroic mirror 129). A beam splitter (e.g., focus dichroic mirror 128) can have a 45 degree angle (e.g., +/−2, 3, or 5 degrees) with respect to the aspheric lens 120 (e.g., an optical axis of the focus dichroic mirror 128 extending toward the objective 106 is at an angle of 45 degrees with respect to an optical axis of the aspheric lens 120). Additionally, another beam splitter (e.g., excitation dichroic mirror 129) can have less than a 40 degree angle with respect to the aspheric lens 120. For example, an optical axis 135 of the excitation dichroic mirror 129, extending toward the objective 106, makes an angle θ with respect to the optical axis of the aspheric lens 120. The angle θ is equal to or less 45, 40, 35, 30, or 25 degrees and/or equal to or greater than 5, 10, 15, or 20 degrees. The angle θ is less than 45 degrees because a distance between the objective 106 and the tube lens 130 is constrained, which makes fitting the focus dichroic mirror 128 and the excitation dichroic mirror 129 both at 45 degree angles between the objective 106 and the tube lens 130 challenging. In some embodiments, the one or more beam splitters can be referred to as mirrors (e.g., a partial mirror). Instead of a beam splitter, a hot mirror or a cold mirror could be used. For example, the excitation dichroic mirror 129 can be a cold mirror (reflecting light with shorter wavelength, such as the excitation light, and passing light of longer wavelengths, such as light from fluorescence of a sample from the flow cell 107). Since excitation light passes through the objective 106, lenses in the objective 106 are made of low fluorescence material (e.g., so excitation light does not cause lenses to fluoresce, which would generate noise at the camera). Low fluorescence material has low absorption and/or low emission from excitation light (e.g., absorption less than 15, 10, 5, or 2 percent at excitation light wavelength(s)). In particular configurations, the objective 106 can transmit radiation in one or more of the ultraviolet (UV), visible (VIS) or infrared (IR) portions of the spectrum. For example, the materials used in the objective can be substantially non-fluorescent in one or more of those ranges of the spectrum.

The flow cell has a coverslip. The coverslip of the flow cell can have a thickness equal to or greater than 0.3, 0.5, 0.7, 0.9, or 1.0 millimeters and/or equal to or less than 2.0, 1.5, or 1.2 millimeters (e.g., 1 millimeter). The objective 106 is configured to image a sample through the coverslip of the flow cell, which is different than an objective used to image through a regular coverslip (e.g., a coverslip 0.17 millimeters thick). Put another way, it does not necessarily follow that an objective used to image through a thin coverslip (e.g., a coverslip 0.17 millimeters thick) could be used to image a flow cell having the coverslip as illustrated in FIG. 3. The first lens 115-1 of the objective is separated by a distance from the flow cell, and the distance from the flow cell is equal to or less than 10, 7, 6, or 5.5 millimeters and/or equal to or greater than 1, 2, 3, or 5 millimeters (e.g., 3.79, 4.25, 5.02, 5.15, 5.22, 5.27, 5.33, or 6.64 millimeters).

In some embodiments, an objective 106 comprises a first doublet lens (e.g., the first lens 115-1) having a first lens and a second lens, wherein: the first lens of the first doublet lens has a concave and a convex surface, and the second lens of the first doublet lens has a concave and a convex surface; a second doublet lens (e.g., the second lens 115-2) having a first lens and a second lens, wherein: the first lens of the second doublet lens has a concave and a convex surface, and the second lens of the second doublet lens has a concave and a convex surface; a third doublet lens (e.g., the third lens 115-3) having a first lens and a second lens, wherein: the first lens of the third doublet lens has two convex surfaces, and the second lens of the third doublet lens has two concave surfaces; a fourth doublet lens (e.g., the fourth lens 115-4) having a first lens and a second lens, wherein: the first lens of the fourth doublet lens has two concave surfaces, and the second lens of the fourth doublet lens has two convex surfaces; an aspheric lens (e.g., the aspheric lens 120) between the third doublet lens and the fourth doublet lens; and an aperture stop (e.g., the aperture stop 125) between the third doublet lens and the fourth doublet lens, wherein the aperture stop is within 25 millimeters of the aspheric lens. The first lens of each doublet lens is closer to the flow cell 107 than the second lens of each doublet lens. Though triplets may be easier to manufacture, triplets can make the optical train of the objective 106 longer. An advantage of a shorter optical train is for the detection system to occupy a relatively small area, for example, for providing a footprint that is appropriate for placement on a typical laboratory bench.

Figure 2:
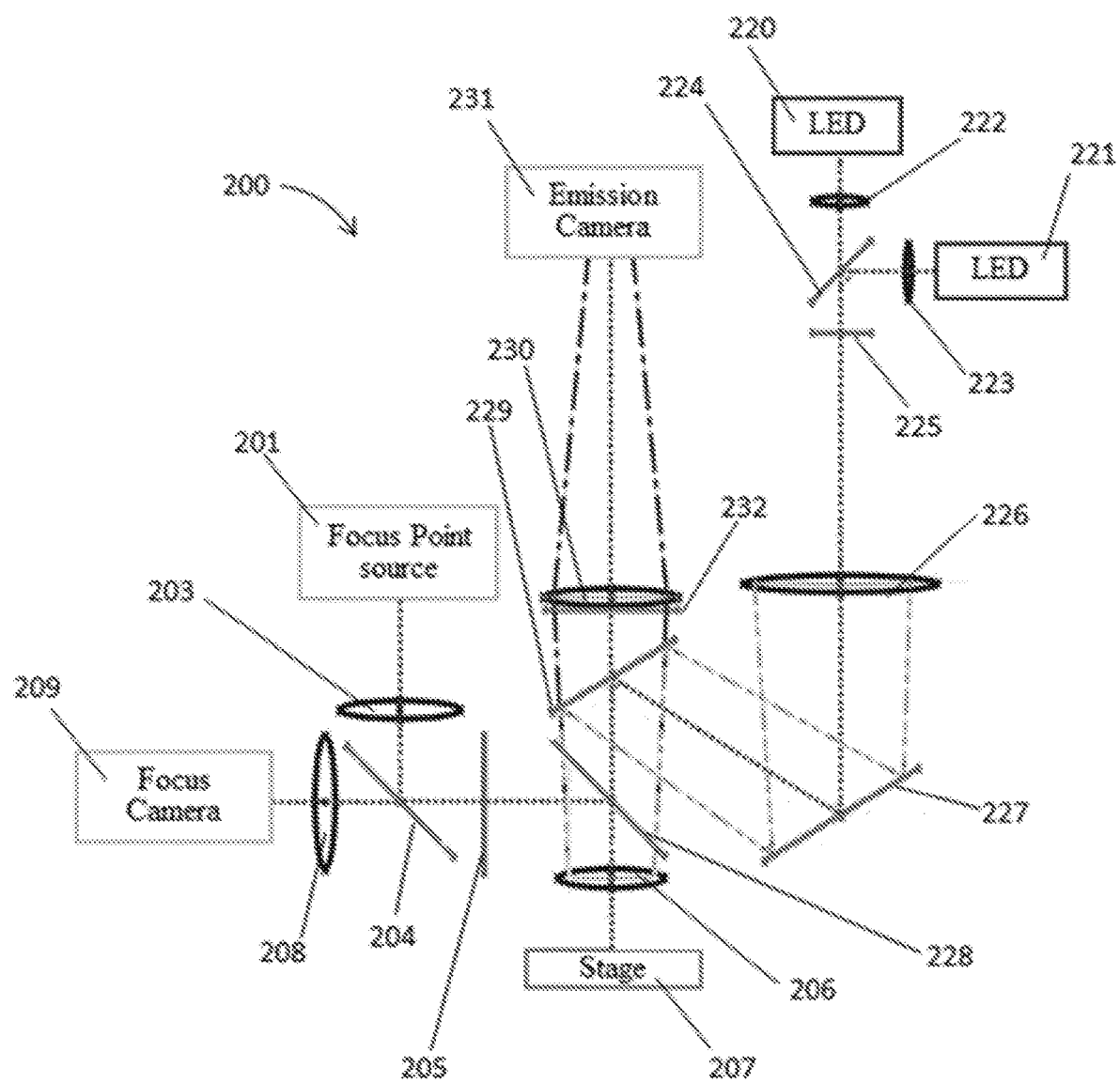
FIG. 2 shows a diagrammatic representation of an epiluminescence detection system having a calibrated focus sensing optical train, a luminescence excitation optical train, and a luminescence detection optical train according to an embodiment of the present invention.

FIG. 2 shows an embodiment of an optical system 200 that includes an analytical optical train that is integrated with a focus sensing optical train. The analytical optical train and the focus sensing optical train both include objective 206 and as such both optical trains are configured to view a specimen on the stage 207. For example, a flow cell, nucleic acid array or other vessel that is placed on the stage 207 can be observed by the analytical optical train and the focus sensing optical train, both, via objective 206. The objective 206 can include the optical elements of objective 106 as shown in FIG. 1. Focus dichroic mirror 228 is configured to reflect radiation between the objective 206 and other components of the focus sensing optical train. Focus dichroic mirror 228 is also configured to transmit radiation between the objective 206 and other components of the analytical optical train. Thus, focus dichroic mirror 228 provides a function of being an intersection or integration point for the analytical optical train and the focus sensing optical train. It will be understood that other optical elements can perform this intersection and integration function as desired to suit a particular layout that achieves a function or provides an advantage set forth herein.

The focus sensing optical train shown in FIG. 2 is configured such that radiation produced by light emitting diode (LED) 201 is collimated by collimator 203 and transmitted to toric beam splitter 204 where at least a portion of the radiation is reflected to calibration beam splitter 205. A portion of the radiation is reflected by the calibration beam splitter 205 such that it passes through toric beam splitter 204, then through an imaging lens 208 to detector 209. The product of this first path is an image on the detector that is indicative of the calibration state of the optical train. The first path in the focus sensing optical train is an example of a calibration sensing path.

As set forth above, a portion of the radiation that was reflected to the calibration beam splitter 205 by the toric beam splitter 204 will be reflected back to the toric beam splitter 204. Another portion of the radiation that was reflected by the toric beam splitter 204 will follow a second path, whereby the radiation passes through the calibration beam splitter 205 to beam splitter 228 which reflects the radiation to objective 206 and then to a specimen that is positioned on the stage 207. As such, the second path can be considered to include the path from radiation source 201, through collimator 203, reflected by toric beam splitter 204, through calibration beam splitter 205, through objective 206 and to the specimen on stage 207. Radiation from the second path can be reflected by the specimen and the reflected radiation can be transmitted along a third path through the objective 206, through calibration beam splitter 205, through toric beam splitter 204, through imaging lens 208 to detector 209. The product of this third path is an image on the detector that is indicative of the focus state of the optical train. The combined second and third paths function as a focus sensing path. The focus sensing optical train can be used for astigmatic focus sensing, for example, methods and systems set forth in U.S. Pat. App. Ser. No. 62/859,886, which is incorporated herein by reference.

Continuing with the exemplary layout shown in FIG. 2, the analytical optical train is configured for epiluminescence, wherein excitation radiation that excites a specimen and emission signals produced by the excited state specimen transmit through a common objective 206. Because the focus sensing optical train also transmits to and from the specimen via the objective 206, the focus errors detected for the system can be related to both the accuracy of detecting luminescence signals from a specimen and the accuracy of exciting a particular focal plane of the specimen. When using optical systems that do not include an excitation path, or that excite a specimen via a fluorescence transmission arrangement that does not utilize epi-illumination, a fluorescence evaluation systems can be configured to share an objective with one of the emission optical path or excitation optical path, depending upon which path is to be evaluated for focus.

The excitation system of FIG. 2 is configured to excite a specimen at two different wavelengths. A first LED 220 produces excitation radiation at a first wavelength and a second LED 221 produces excitation radiation at a second wavelength. The excitation radiation from first LED 220 and second LED 221 is transmitted by condenser lens 222 and condenser lens 223, respectively, to excitation combiner 224 which converges the two excitation paths. The excitation paths then pass through dual band pass filter 225 and excitation lens 226 to reflector 227, which in turn reflects the excitation radiation to excitation dichroic mirror 229. The excitation radiation is reflected by excitation dichroic mirror 229 then passes through focus dichroic mirror 228 to objective 206 and to a specimen on stage 207.

The exemplary system in FIG. 2 includes two excitation sources. It will be understood, that a similar system can be modified for use with only 1 excitation source or with greater than 2 excitation sources. For example, including up to four excitation sources can be beneficial for applications that distinguish 4 different nucleotide types that may be present in a nucleic acid based on each being labeled with one of four different luminophores that are distinguished based on different responses to different excitation wavelengths. However, fewer than four different luminophores can be used to distinguish four different nucleotide types, for example, as set forth in U.S. Pat. No. 10,161,003, which is incorporated herein by reference.

The analytical optical train also includes optical components that direct luminescent signals from the specimen on stage 207 to emission camera 231. Emitted radiation from the specimen can be collected by objective 206 and transmitted through focus dichroic mirror 228, then through excitation dichroic mirror 229, then through emission dual bandpass 232 and imaging tube 230 to emission camera 231. In this exemplary configuration, emission from luminophores excited at two wavelengths can be detected by a single camera. The system can be readily modified to include two or more cameras by introducing splitting optic into the emission detection path. For example, a system that is used for detecting nucleic acids can include up to four different cameras to distinguish labels for four different nucleotide types when detecting nucleic acids.

Several aspects of calibrated focus sensing have been exemplified herein with regard to detection of astigmatic radiation. It will be understood, that other properties of radiation can provide a basis for evaluating focus and calibration of an optical system. For example, a focus sensing systems can be configured with an optical train that transmits polarized light in a way that changes in optical train will manifest as observable changes in polarization of the light that can, in turn be correlated with focus position and calibration of the focus systems. More specifically, the optical path of FIG. 2 can be modified as follows. Toric beam splitter 204 can be replaced with a polarizing beam splitter that reflects radiation of one polarization and transmits radiation of a second polarization. The radiation source can be a source of unpolarized radiation (e.g. an LED) or a laser oriented to have two polarizations. Continuing with the modified optical path, a polarization rotator can be added to the optical train to convert polarization from the transmitted polarization state to the reflected polarization state. A second polarization rotator can be added to the sensing arm of the optical path to convert polarization for the transmitted radiation through the polarization beam splitter to the detector. These configurations and others are set forth in U.S. Pat. App. Ser. No. 62/859,886, which is incorporated herein by reference.

In particular configurations, a system or method set forth herein can employ optical sub-systems or components used in nucleic acid sequencing systems. Several such detection systems are configured for optical detection, for example, detection of fluorescent signals. Examples of detection systems and components thereof that can be used to detect a vessel herein are described, for example, in US Pat. App. Pub. No. 2010/0111768 A1 or U.S. Pat. Nos. 7,329,860; 8,951,781 or 9,193,996, each of which is incorporated herein by reference. Other detection systems include those commercialized for nucleic acid sequencing such as those provided by Illumina™, Inc. (e.g. HiSeg™, MiSeg™, NextSeg™, or NovaSeg™ systems), Life Technologies™ (e.g. ABI PRISM™, or SOLiD™ systems), Pacific Biosciences (e.g. systems using SMRT™ Technology such as the Sequel™ or RS II™ systems), or Qiagen (e.g. Genereader™ system). Other useful detectors are described in U.S. Pat. Nos. 5,888,737; 6,175,002; 5,695,934; 6,140,489; or 5,863,722; or US Pat. Pub. Nos. 2007/007991 A1, 2009/0247414 A1, or 2010/0111768; or WO2007/123744, each of which is incorporated herein by reference in its entirety. Particularly useful nucleic acid sequencing systems that can be modified to employ optical components set forth herein are provided in US Pat. App. Pub. No. 2019/0055598 A1 and U.S. Pat App. Ser. No. 62/807,934, each of which is incorporated herein by reference.

Accordingly, the present disclosure provides a nucleic acid sequencing system that includes (a) a stage configured to hold a specimen; (b) an optical train including a radiation source, calibration optic, objective and detector, the optical train forming a first path wherein radiation from the radiation source is directed to the calibration optic and then a first portion of the radiation is directed to the detector, thereby forming a first image on the detector, wherein a second portion of the radiation follows a second path from the calibration optic then through the objective to the specimen, wherein the optical train forms a third path wherein radiation reflected from the specimen is transmitted through the objective, then to the detector, thereby forming a second image on the detector, and wherein the radiation that forms the first image is astigmatic; and (c) a luminescence optical train for directing radiation from an excitation radiation source through the objective to the specimen and for directing luminescent emission radiation from the specimen through the objective to a luminescence detector.

In particular configurations, a nucleic acid sequencing system can include (a) a stage configured to hold a specimen; (b) an optical train comprising a radiation source, collimator, primary beam splitter, calibration beam splitter, objective and detector, the optical train forming a first path wherein radiation from the radiation source is collimated by the collimator, then transmitted to the primary beam splitter, then to the calibration beam splitter, then a first portion of the radiation continues on the first path from the calibration beam splitter to the primary beam splitter, then to the detector, thereby forming a first image on the detector, wherein a second portion of the radiation follows a second path from the calibration beam splitter then through the objective to the specimen, wherein the optical train forms a third path wherein radiation from the specimen is transmitted through the objective, then through the calibration beam splitter, then through the primary beam splitter, then to the detector, thereby forming a second image on the detector, and wherein the primary beam splitter has a toric surface for transmitting radiation from the collimator to the calibration beam splitter, or the optical train includes an astigmatic lens between the radiation source and the calibration beam splitter; and (c) a luminescence optical train for directing radiation from an excitation radiation source through the objective to the specimen and for directing luminescent emission radiation from the specimen through the objective to a luminescence detector.

A sequencing system or other detection system can be configured to have a radiation source that is used for both a focus sensing optical train and an analytical optical train. Accordingly, the radiation source can be used to produce both a reflection that is used for focus sensing and to produce luminescence emission for analytical analysis of the specimen being focused. Alternatively, separate radiation sources can be used, one for a focus sensing optical train (e.g. to produce a reflection that is evaluated to determine focus), and another for an analytical optical train (e.g. to excite luminophores that produce luminescent emission used for analysis of a specimen).

A sequencing system or other detection system can be configured to have a detector that is used for both focus sensing of a specimen and for analytical evaluation of the specimen. Accordingly, the detector can be used to detect both a reflection that is used for focus sensing and to detect luminescence emission for analytical analysis of the specimen being focused. Alternatively, separate detectors can be used, one for a focus sensing optical train (e.g. to observe a reflection that is evaluated to determine focus), and another for an analytical optical train (e.g. to observe emission from luminophores that indicate a characteristic of interest for a specimen).

Several systems and methods have been exemplified herein using a flow cell as a specimen or as a vessel for presenting a specimen to be detected. Any of a variety of vessels can be used in an system or method set forth herein. A flow cell can be useful, especially for nucleic acid sequencing applications or other applications that utilize repeated reagent deliveries. A flow cell can include a solid support to which one or more target analytes or reagents are attached. A particularly useful solid support (whether used in a flow cell or other vessel) is one having an array of sites. Arrays provide the advantage of facilitating multiplex detection. For example, different reagents or analytes (e.g. cells, nucleic acids, proteins, candidate small molecule therapeutics etc.) can be attached to an array via linkage of each different analyte to a particular site of the array. Exemplary array substrates that can be useful include, without limitation, a BeadChip™ Array available from Illumina, Inc. (San Diego, Calif.) or arrays such as those described in U.S. Pat. Nos. 6,266,459; 6,355,431; 6,770,441; 6,859,570; or 7,622,294; or PCT Publication No. WO 00/63437, each of which is incorporated herein by reference. Further examples of commercially available array substrates that can be used include, for example, an Affymetrix GeneChip™ array. A spotted array substrate can also be used according to some embodiments. An exemplary spotted array is a CodeLink™ Array available from Amersham Biosciences. Another array that is useful is one that is manufactured using inkjet printing methods such as SurePrint™ Technology available from Agilent Technologies.

Other useful array substrates include those that are used in nucleic acid sequencing applications. For example, arrays that are used to create attached amplicons of genomic fragments (often referred to as clusters) can be particularly useful. Examples of substrates that can be modified for use for sequencing or other applications set forth herein or known in the art include those described in Bentley et al., Nature 456:53-59 (2008), PCT Pub. Nos. WO 91/06678; WO 04/018497 or WO 07/123744; U.S. Pat. Nos. 7,057,026; 7,211,414; 7,315,019; 7,329,492 or 7,405,281; or U.S. Pat. App. Pub. No. 2008/0108082 A1, each of which is incorporated herein by reference.

An array can have sites that are separated by less than 100 µm, 50 µm, 10 µm, 5 µm, 1 µm, or 0.5 µm. In particular embodiments, sites of an array can each have an area that is larger than about 100 $nm^2$ m, 250 $nm^2$, 500 $nm^2$, 1 $µm^2$, 2.5 $µm^2$, 5 $µm^2$, 10 $µm^2$, 100 $µm^2$, or 500 $µm^2$. Alternatively or additionally, sites of an array can each have an area that is smaller than about 1 mm$^2$, 500 µm$^2$, 100 µm$^2$, 25 µm$^2$, 10 µm$^2$, 5 µm$^2$, 1 µm$^2$, 500 nm$^2$, or 100 nm$^2$.

Indeed, a site can have a size that is in a range between an upper and lower limit selected from those exemplified above. An array can have sites at any of a variety of densities including, for example, at least about 10 sites/cm$^2$, 100 sites/cm$^2$, 500 sites/cm$^2$, 1,000 sites/cm$^2$, 5,000 sites/cm$^2$, 10,000 sites/cm$^2$, 50,000 sites/cm$^2$, 100,000 sites/cm$^2$, 1,000,000 sites/cm$^2$, 5,000,000 sites/cm$^2$, or higher. An embodiment of the systems or methods set forth herein can be used to image an array at a resolution sufficient to distinguish sites at the above densities or site separations.

Several embodiments utilize optical detection of analytes in a flow cell. Accordingly, a flow cell can include one or more channels each having at least one transparent window. In particular embodiments, the window can be transparent to radiation in a particular spectral range including, but not limited to x-ray, ultraviolet (UV), visible (VIS), infrared (IR), microwave and/or radio wave radiation. In some cases, analytes are attached to an inner surface of the window(s). Alternatively or additionally, one or more windows can provide a view to an internal substrate to which analytes are attached. Exemplary flow cells and physical features of flow cells that can be useful in a method or system set forth herein are described, for example, in US Pat. App. Pub. No. 2010/0111768 A1, WO 05/065814 or US Pat. App. Pub. No. 2012/0270305 A1, each of which is incorporated herein by reference in its entirety.

Exemplary reaction vessels (e.g. flow cells) and fluidic components that can be modified, in accordance with teachings herein, for use in combination with detection components of the present disclosure are described in commonly owned US Pat. App. Pub. No. 2018/0280975 A1, which is incorporated herein by reference. Other fluidic components that are useful, particularly for cyclic reactions such as nucleic acid sequencing reactions, are set forth in US Pat. App. Pub. Nos. 2009/0026082 A1; 2009/0127589 A1; 2010/0111768 A1; 2010/0137143 A1; or 2010/0282617 A1; or U.S. Pat. Nos. 7,329,860; 8,951,781 or 9,193,996, each of which is incorporated herein by reference.

As will be evident from the examples set forth herein, a vessel can be open (e.g. a well of a multi-well plate, surface of a chip, or surface of a sheet) or the vessel can be enclosed (e.g. a lane of a flow cell). It will be understood that, wells of a multi-well plate can optionally be covered to create an enclosed vessel and similarly a sheet, belt, tape or ribbon can have multiple layers such that an internal lumen occurs between layers. Alternatively, a vessel can have one or more open structures such as a trough, well or other concave structure that contains a fluid. A vessel can also have a convex or protruding structure such as a post or ridge, and optionally individual protrusions can each be attached to one or more analyte that is to be detected or manipulated.

A detection system or other apparatus of the present disclosure can include a fluidics system for delivering reagents to a vessel that is to be detected. Accordingly, one or more reservoirs can be fluidically connected to an inlet valve of the vessel. The system can further include a pressure supply for driving reagents from reservoirs to the vessel. The system can include a waste reservoir that is fluidically connected to the vessel to remove spent reagents. Taking as an example an embodiment where the vessel is a flow cell, reagents can be delivered via pump to the flow cell through the inlet and then the reagents can flow through the flow cell outlet to a waste reservoir. The reservoirs can include reagents for any of a variety of analytical procedures including, but not limited to nucleic acid sequencing, nucleic acid genotyping, nucleic acid expression analysis, protein sequencing, protein binding analysis (e.g. ELISA), small molecule receptor binding, protein phosphorylation analysis, nucleic acid synthesis or protein synthesis. Alternatively or additionally, the reservoirs can include reagents for a preparative process. Exemplary preparative processes include, but are not limited to, nucleic acid synthesis, peptide synthesis, assembly of oligonucleotides into genes, photolithography, nanofabrication or microfabrication (e.g. via laser etching), laser ablation, or the like.

A fluidic system can include at least one manifold and/or at least one valve for directing reagents from reservoirs to a vessel where detection occurs. Manifolds are particularly useful in sequencing instruments due to the relatively large number of different reagents that are delivered during a sequencing protocol. Exemplary protocols and useful reagents are set forth in further detail below and in references that are incorporated herein by reference. Fluid flow from the reservoirs can be selected via valves such as a solenoid valve (e.g. those made by Takasago Electric, Japan), ball valve, diaphragm valve or rotary valve.

The present disclosure provides systems and methods that are particularly useful for performing cyclical reactions due to the speed and accuracy of focus sensing (and if desired, adjustment) provided and due to the combination of high magnification and wide field of detection provided by objective configurations set forth herein. Each cycle can include delivering reagents for the reaction to a flow cell or other vessel where, optionally, the reaction, or products of the reaction, will be observed. Each cycle can further include detection of the vessel using systems or methods set forth herein. The methods are exemplified herein in the context of a nucleic acid sequencing reaction. However, those skilled in the art will understand from the teaching herein how to modify the methods, and the systems, for other cyclical reactions such as nucleic acid synthesis reactions, peptide sequencing reactions, peptide synthesis reactions, combinatorial small molecule synthesis reactions or the like. However, the method need not be cyclical and can instead be carried out in a non-repetitive configuration, for example, to observe a single reaction or phenomenon.

Particularly useful sequencing reactions are Sequencing By Binding™ (SBB™) reactions as described in commonly owned US Pat. App. Pub. Nos. 2017/0022553 A1, 2018/0044727 A1, 2018/0187245 A1 or 2018/0208983 A1, each of which is incorporated herein by reference. Generally, methods for determining the sequence of a template nucleic acid molecule can be based on formation of a ternary complex (between polymerase, primed nucleic acid and cognate nucleotide) under specified conditions. The method can include an examination phase followed by a nucleotide incorporation phase.

The examination phase can be carried out in a flow cell (or other vessel), the flow cell containing at least one template nucleic acid molecule primed with a primer by delivering to the flow cell reagents to form a first reaction mixture. The reaction mixture can include the primed template nucleic acid, a polymerase and at least one nucleotide type. Interaction of polymerase and a nucleotide with the primed template nucleic acid molecule(s) can be observed under conditions where the nucleotide is not covalently added to the primer(s); and the next base in each template nucleic acid can be identified using the observed interaction of the polymerase and nucleotide with the primed template nucleic acid molecule(s). The interaction between the primed template, polymerase and nucleotide can be detected in a variety of schemes. For example, the nucleotides can contain a detectable label. Each nucleotide can have a distinguishable label with respect to other nucleotides. Alternatively, some or all of the different nucleotide types can have the same label and the nucleotide types can be distinguished based on separate deliveries of different nucleotide types to the flow cell. In some embodiments, the polymerase can be labeled. Polymerases that are associated with different nucleotide types can have unique labels that distinguish the type of nucleotide to which they are associated. Alternatively, polymerases can have similar labels and the different nucleotide types can be distinguished based on separate deliveries of different nucleotide types to the flow cell. Detection can be carried out using a system or method set forth herein.

During the examination phase, discrimination between correct and incorrect nucleotides can be facilitated by ternary complex stabilization. A variety of conditions and reagents can be useful. For example, the primer can contain a reversible blocking moiety that prevents covalent attachment of nucleotide; and/or cofactors that are required for extension, such as divalent metal ions, can be absent; and/or inhibitory divalent cations that inhibit polymerase-based primer extension can be present; and/or the polymerase that is present in the examination phase can have a chemical modification and/or mutation that inhibits primer extension; and/or the nucleotides can have chemical modifications that inhibit incorporation, such as 5' modifications that remove or alter the native triphosphate moiety. The examination phase can include detection systems and methods set forth herein.

The extension phase can then be carried out by creating conditions in the flow cell where a nucleotide can be added to the primer on each template nucleic acid molecule. In some embodiments, this involves removal of reagents used in the examination phase and replacing them with reagents that facilitate extension. For example, examination reagents can be replaced with a polymerase and nucleotide(s) that are capable of extension. Alternatively, one or more reagents can be added to the examination phase reaction to create extension conditions. For example, catalytic divalent cations can be added to an examination mixture that was deficient in the cations, and/or polymerase inhibitors can be removed or disabled, and/or extension competent nucleotides can be added, and/or a deblocking reagent can be added to render primer(s) extension competent, and/or extension competent polymerase can be added.

It will be understood that any of a variety of nucleic acid sequencing reactions can be carried out using a system or method of the present disclosure. Other exemplary sequencing methods are set forth below.

Sequencing-by-synthesis (SBS) techniques can be used. SBS generally involves the enzymatic extension of a nascent primer through the iterative addition of nucleotides against a template strand to which the primer is hybridized. Briefly, SBS can be initiated by contacting target nucleic acids, attached to sites in a vessel, with one or more labeled nucleotides, DNA polymerase, etc. Those sites where a primer is extended using the target nucleic acid as template will incorporate a labeled nucleotide that can be detected. Detection can employ a detection system or method set forth herein. Optionally, the labeled nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the vessel (before or after detection occurs). Washes can be carried out between the various delivery steps. The cycle can be performed n times to extend the primer by n nucleotides, thereby detecting a sequence of length n. Exemplary SBS procedures, reagents and detection components that can be readily adapted for use with a detection system produced by the methods of the present disclosure are described, for example, in Bentley et al., *Nature* 456:53-59 (2008), WO 04/018497; WO 91/06678; WO 07/123744; U.S. Pat. Nos. 7,057,026; 7,329,492; 7,211,414; 7,315,019 or 7,405,281, and US Pat. App. Pub. No. 2008/0108082 A1, each of which is incorporated herein by reference. Also useful are SBS methods that are commercially available from Illumina, Inc. (San Diego, Calif.).

Other sequencing procedures can be used, such as pyrosequencing. Pyrosequencing detects the release of inorganic pyrophosphate (PPi) as nucleotides are incorporated into a nascent primer hybridized to a template nucleic acid strand (Ronaghi, et al., *Analytical Biochemistry* 242 (1), 84-9 (1996); Ronaghi, *Genome Res.* 11 (1), 3-11 (2001); Ronaghi et al. *Science* 281 (5375), 363 (1998); U.S. Pat. Nos. 6,210,891; 6,258,568 and 6,274,320, each of which is incorporated herein by reference). In pyrosequencing, released PPi can be detected by being converted to adenosine triphosphate (ATP) by ATP sulfurylase, and the resulting ATP can be detected via luciferase-produced photons. Thus, the sequencing reaction can be monitored via a luminescence detection system that is configured to focus and/or detect a vessel using systems and methods set forth herein.

Sequencing-by-ligation reactions are also useful including, for example, those described in Shendure et al. Science 309:1728-1732 (2005); U.S. Pat. No. 5,599,675; or U.S. Pat. No. 5,750,341, each of which is incorporated herein by reference. Some embodiments can include sequencing-by-hybridization procedures as described, for example, in Bains et al., Journal of Theoretical Biology 135 (3), 303-7 (1988); Drmanac et al., Nature Biotechnology 16, 54-58 (1998); Fodor et al., Science 251 (4995), 767-773 (1995); or WO 1989/10977, each of which is incorporated herein by reference. In both sequencing-by-ligation and sequencing-by-hybridization procedures, primers that are hybridized to nucleic acid templates are subjected to repeated cycles of extension by oligonucleotide ligation. Typically, the oligonucleotides are fluorescently labeled and can be detected to determine the sequence of the template, for example, using a system or method set forth herein for focusing and/or detection.

Steps for the above sequencing methods can be carried out cyclically. For example, examination and extension steps of an SBB™ method can be repeated such that in each cycle a single next correct nucleotide is examined (i.e. the next correct nucleotide being a nucleotide that correctly binds to the nucleotide in a template nucleic acid that is located immediately 5' of the base in the template that is hybridized to the 3'-end of the hybridized primer) and, subsequently, a single next correct nucleotide is added to the primer. Any number of cycles of a sequencing method set forth herein can be carried out including, for example, at least 1, 2, 5, 10, 20, 25, 30, 40, 50, 75, 100, 150 or more cycles. Alternatively or additionally, no more than 150, 100, 75, 50, 40, 30, 25, 20, 10, 5, 2 or 1 cycles are carried out.

Nucleic acid template(s), to be sequenced, can be added to a vessel using any of a variety of known methods. In some embodiments, a single nucleic acid molecule is to be sequenced. The nucleic acid molecule can be delivered to a vessel and can optionally be attached to a surface in the vessel. In some embodiments, the molecule is subjected to single molecule sequencing. Alternatively, multiple copies of the nucleic acid can be made, and the resulting ensemble can be sequenced. For example, the nucleic acid can be amplified on a surface (e.g. on the inner wall of a flow cell) using techniques set forth in further detail below.

In multiplex embodiments, a variety of different nucleic acid molecules (i.e. a population having a variety of different sequences) are sequenced. The molecules can optionally be attached to a surface in a vessel. The nucleic acids can be attached at unique sites on the surface and single nucleic acid molecules that are spatially distinguishable one from the other can be sequenced in parallel. Alternatively, the nucleic acids can be amplified on the surface to produce a plurality of surface attached ensembles. The ensembles can be sequenced in parallel and detected in a spatially distinguishable way using methods and systems of the present disclosure.

A method set forth herein can use any of a variety of amplification techniques in a vessel. Exemplary techniques that can be used include, but are not limited to, polymerase chain reaction (PCR), rolling circle amplification (RCA), multiple displacement amplification (MDA), bridge amplification, or random prime amplification (RPA). In particular embodiments, one or more primers used for amplification can be attached to a surface in a vessel. In such embodiments, extension of the surface-attached primers along template nucleic acids will result in copies of the templates being attached to the surface. Methods that result in one or more sites on a solid support, where each site is attached to multiple copies of a particular nucleic acid template, can be referred to as "clustering" methods.

In PCR embodiments, one or both primers used for amplification can be attached to a surface. Formats that utilize two species of attached primer are often referred to as bridge amplification because double stranded amplicons form a bridge-like structure between the two attached primers that flank the template sequence that has been copied. Exemplary reagents and conditions that can be used for bridge amplification are described, for example, in U.S. Pat. No. 5,641,658 or 7,115,400; U.S. Patent Pub. Nos. 2002/0055100 A1, 2004/0096853 A1, 2004/0002090 A1, 2007/0128624 A1 or 2008/0009420 A1, each of which is incorporated herein by reference. PCR amplification can also be carried out with one of the amplification primers attached to the surface and the second primer in solution. An exemplary format that uses a combination of one solid phase-attached primer and a solution phase primer is known as primer walking and can be carried out as described in U.S. Pat. No. 9,476,080, which is incorporated herein by reference. Another example is emulsion PCR which can be carried out as described, for example, in Dressman et al., *Proc. Natl. Acad. Sci. USA* 100:8817-8822 (2003), WO 05/010145, or U.S. Patent Pub. Nos. 2005/0130173 A1 or 2005/0064460 A1, each of which is incorporated herein by reference.

RCA techniques can be used in a method set forth herein. Exemplary reagents that can be used in an RCA reaction and principles by which RCA produces amplicons are described, for example, in Lizardi et al., *Nat. Genet.* 19:225-232 (1998) or US Pat. App. Pub. No. 2007/0099208 A1, each of which is incorporated herein by reference. Primers used for RCA can be in solution or attached to a surface in a flow cell.

MDA techniques can also be used in a method of the present disclosure. Some reagents and useful conditions for MDA are described, for example, in Dean et al., *Proc Natl. Acad. Sci. USA* 99:5261-66 (2002); Lage et al., *Genome Research* 13:294-307 (2003); Walker et al., *Molecular Methods for Virus Detection*, Academic Press, Inc., 1995; Walker et al., *Nucl. Acids Res.* 20:1691-96 (1992); or U.S. Pat. Nos. 5,455,166; 5,130,238; or 6,214,587, each of which is incorporated herein by reference. Primers used for MDA can be in solution or attached to a surface in a vessel.

In particular embodiments, a combination of the above-exemplified amplification techniques can be used. For example, RCA and MDA can be used in a combination wherein RCA is used to generate a concatemeric amplicon in solution (e.g. using solution-phase primers). The amplicon can then be used as a template for MDA using primers that are attached to a surface in a vessel. In this example, amplicons produced after the combined RCA and MDA steps will be attached in the vessel. The amplicons will generally contain concatemeric repeats of a target nucleotide sequence.

Nucleic acid templates that are used in a method or composition herein can be DNA such as genomic DNA, synthetic DNA, amplified DNA, complementary DNA (cDNA) or the like. RNA can also be used such as mRNA, ribosomal RNA, tRNA or the like. Nucleic acid analogs can also be used as templates herein. Thus, a mixture of nucleic acids used herein can be derived from a biological source, synthetic source or amplification product. Primers used herein can be DNA, RNA or analogs thereof.

Exemplary organisms from which nucleic acids can be derived include, for example, those from a mammal such as a rodent, mouse, rat, rabbit, guinea pig, ungulate, horse, sheep, pig, goat, cow, cat, dog, primate, human or non-human primate; a plant such as *Arabidopsis thaliana*, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, honey bee or spider; a fish such as zebrafish; a reptile; an amphibian such as a frog or *Xenopus laevis*; a dictyostelium discoideum; a fungi such as *Pneumocystis carinii, Takifugu rubripes*, yeast, *Saccharamoyces cerevisiae* or *Schizosaccharomyces pombe*; or a *Plasmodium falciparum*. Nucleic acids can also be derived from a prokaryote such as a bacterium, *Escherichia coli*, staphylococci or *Mycoplasma pneumoniae*; an archae; a virus such as Hepatitis C virus or human immunodeficiency virus; or a viroid. Nucleic acids can be derived from a homogeneous culture or population of the above organisms or alternatively from a collection of several different organisms, for example, in a community or ecosystem. Nucleic acids can be isolated using methods known in the art including, for example, those described in Sambrook et al., *Molecular Cloning: A Laboratory Manual,* 3rd edition, Cold Spring Harbor Laboratory, New York (2001) or in Ausubel et al., *Current Protocols in Molecular Biology,* John Wiley and Sons, Baltimore, Md. (1998), each of which is incorporated herein by reference. Cells, tissues, biological fluids, proteins and other samples can be obtained from these organisms and detected using a system or method set forth herein.

A template nucleic acid can be obtained from a preparative method such as genome isolation, genome fragmentation, gene cloning and/or amplification. The template can be obtained from an amplification technique such as polymerase chain reaction (PCR), rolling circle amplification (RCA), multiple displacement amplification (MDA) or the like. Exemplary methods for isolating, amplifying and fragmenting nucleic acids to produce templates for analysis on an array are set forth in U.S. Pat. No. 6,355,431 or 9,045,796, each of which is incorporated herein by reference. Amplification can also be carried out using a method set forth in Sambrook et al., *Molecular Cloning: A Laboratory Manual,* 3rd edition, Cold Spring Harbor Laboratory, New York (2001) or in Ausubel et al., *Current Protocols in Molecular Biology*, John Wiley and Sons, Baltimore, Md. (1998), each of which is incorporated herein by reference.

The systems and methods of the present disclosure have been exemplified in the context of use for nucleic acid sequencing reactions. The systems and methods can be used for other analytical applications as well. Generally, analytical applications that are carried out in scanning microscopes can be applied to systems and methods of the present disclosure. For example, the methods or systems can be configured to scan microarrays that are used for analyzing enzyme activity, binding of ligands to receptors, binding of complementary nucleic acids to each other, presence of mutations (such as single nucleotide polymorphisms (SNPs)) in nucleic acids, expression level for RNA species. Microarrays that are detected via optical labels, such as fluorophores, are particularly applicable. Larger biological samples such as cells or tissues can be detected using a method or system herein. Other uses include evaluation of manufactured products for which quality or other characteristics are evaluated via microscopic scanning. Exemplary products include, but are not limited to, computer chips, sensors, electronic components and other devices that are microfabricated or nanofabricated. Tests known in the art of molecular diagnostics can be modified for use in a system or method set forth herein such as binding assays (e.g. enzyme-linked immunosorbent assay (ELISA)), real time polymerase chain reaction assays and the like. Real time polymerase chain reaction and quantitative polymerase chain reaction methods that employ optical detection techniques can employ focus sensing systems and methods set forth herein.

In some embodiments, the objective 106 in FIG. 1 is the same as the objective 206 in FIG. 2 and the description provided in relation to objective 106 is applicable to objective 206 as appropriate and the description provided in relation to objective 206 is applicable to objective 106 as appropriate; the flow cell 107 can be positioned on the stage 207 and the description provided in relation to flow cell 107 is applicable to stage 207 as appropriate and the description provided in relation to stage 207 is applicable to flow cell 107 as appropriate; the focus dichroic mirror 128 is the same as the focus dichroic mirror 228 and the description provided in relation to focus dichroic mirror 128 is applicable to focus dichroic mirror 228 as appropriate and the description provided in relation to focus dichroic mirror 228 is applicable to focus dichroic mirror 128 as appropriate; the excitation dichroic mirror 129 is the same as the excitation dichroic mirror 229 and the description provided in relation to excitation dichroic mirror 129 is applicable to excitation dichroic mirror 229 as appropriate and the description provided in relation to excitation dichroic mirror 229 is applicable to excitation dichroic mirror 129 as appropriate; the tube lens 130 is the same as the imaging tube 230 and the description provided in relation to tube lens 130 is applicable to imaging tube 230 as appropriate and the description provided in relation to imaging tube 230 is applicable to tube lens 130 as appropriate; and/or the sensor 110 is part of the emission camera 231.

Figure 3A:
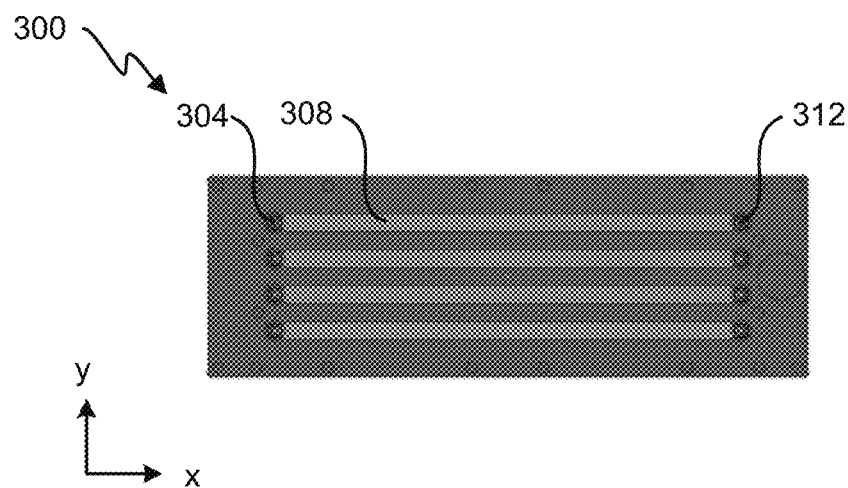
FIGS. 3A and 3B illustrate an embodiment of a flow cell.
Figure 3B:
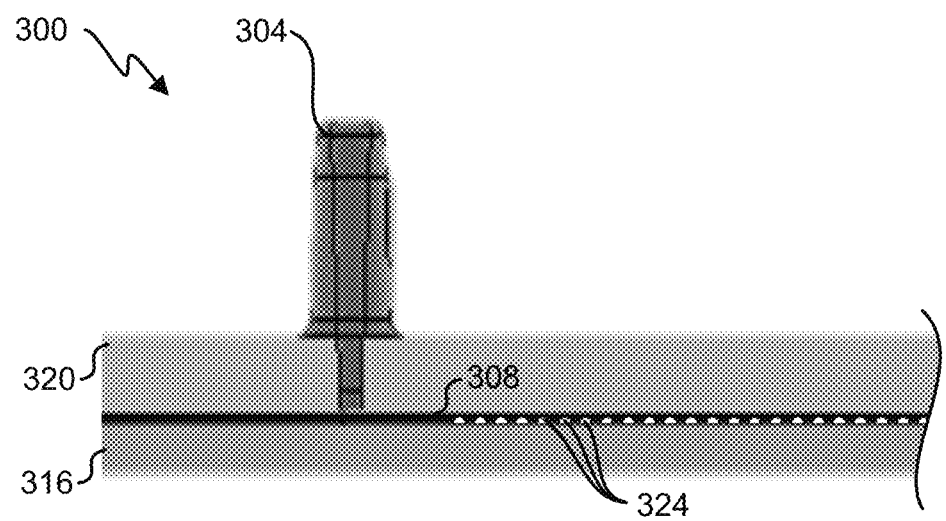

FIGS. 3A and 3B illustrate an embodiment of a flow cell 300. FIG. 3A is a top view of the flow cell 300. FIG. 3B is a cross-sectional view of the flow cell 300. In FIG. 3A, fluid flows from an inlet port 304, through a flowcell lane 308, and exits through an outlet port 312. In FIG. 3A, there are a plurality of inlet ports, flowcell lanes, and outlet ports.

In FIG. 3B, a cross section of the flow cell 300 in an x/z plane is shown. Fluid flows into the inlet port 304 and to the flowcell lane 308. Fluid is confined in the z direction by a substrate 316 and a coverslip 320. The coverslip 320 is sometimes referred to as the portside because light emitted from the flow cell 300 through the coverslip 320 is imaged (e.g., by optical system 100). In some embodiment, the flow cell 300 is mounted to the stage 207.

The substrate 316 is sometimes referred to as a solid support (e.g., the substrate 316 is rigid). An array of sites 324, with one or more analytes or reagents attach to a surface of the substrate 316 (e.g., to a top surface of the substrate 316), is shown. Accordingly, the array of sites 324 is inside the flow cell 300. In some embodiments, the substrate 316 is made of glass. The array of sites 324 is imaged while attached to the substrate 316.

Figure 4:
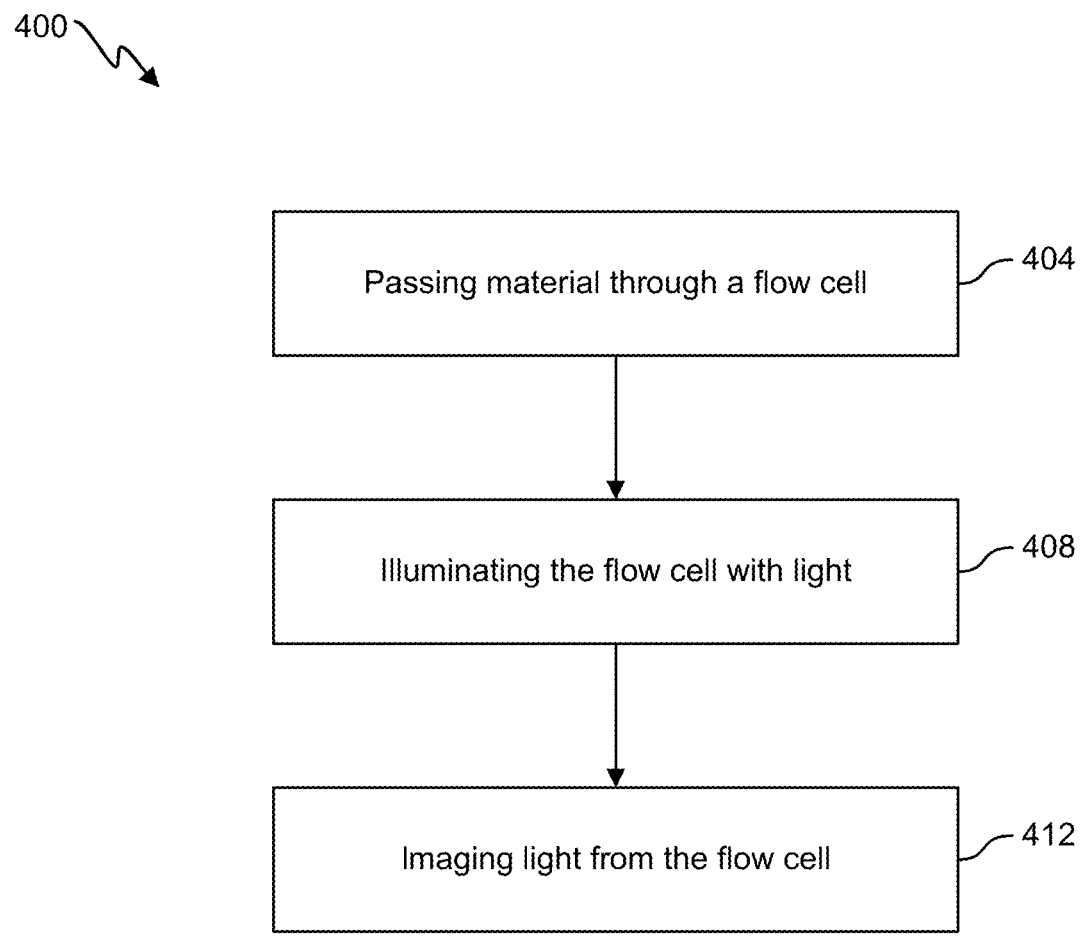
FIG. 4 illustrates a flowchart of an embodiment of a process for DNA sequencing.

FIG. 4 illustrates a flowchart of an embodiment of a process 400 for DNA sequencing. Process 400 begins in step 404 with passing material through a flow cell (e.g., flow cell 300). The material comprises a specimen for DNA sequencing. The flow cell is illuminated with light, step 408. For example, excitation light from an LED is coupled into the objective 206 and directed to the flow cell 107 by the objective 206. In step 412, light is imaged from the flow cell. For example, the emission camera 231 images the flow cell 107 through the objective 206. The objective 206 comprises a plurality of lenses having simple surfaces (e.g., lenses 115); an aperture stop (e.g., the aperture stop 125); and an aspheric lens (e.g., the aspheric lens 120). The aspheric lens is positioned within 25 millimeters of the aperture stop. In some embodiments the aspheric lens is adjacent to the aperture stop (e.g., no other optical elements are between the aspheric lens 120 and the aperture stop 125).

Terms used herein will be understood to take on their ordinary meaning in the relevant art unless specified otherwise. The term "comprising" is intended herein to be open-ended, including not only the recited elements, but further encompassing any additional elements. The term "each," when used in reference to a collection of items, is intended to identify an individual item in the collection but does not necessarily refer to every item in the collection. Exceptions can occur if explicit disclosure or context clearly dictates otherwise.

As used herein, the term "array" refers to a collection of molecules that is attached to one or more solid supports such that the molecules at one site can be distinguished from molecules at other sites. An array can include different molecules that are each located at different addressable sites on a solid support. Alternatively, an array can include separate solid supports each functioning as a site that bears a different molecule, wherein the different molecules can be identified according to the locations of the solid supports on a surface to which the solid supports are attached, or according to the locations of the solid supports in a liquid such as a fluid stream. The molecules of the array can be, for example, nucleotides, nucleic acid primers, nucleic acid templates or nucleic acid enzymes such as polymerases, ligases, exonucleases or combinations thereof.

As used herein, the term "site," when used in reference to an array, means a location in an array where a particular molecule is present. A site can contain only a single molecule or it can contain a population of several molecules of the same species (i.e. an ensemble of the molecules). Alternatively, a site can include a population of molecules that includes different species (e.g. a population of ternary complexes having different template sequences). Sites of an array are typically discrete. The discrete sites can be contiguous or they can have interstitial spaces between each other. An array useful herein can have, for example, sites that are separated by less than 100 microns, 50 microns, 10 microns, 5 microns, 1 micron, or 0.5 micron. Alternatively or additionally, an array can have sites that are separated by greater than 0.5 micron, 1 micron, 5 microns, 10 microns, 50 microns or 100 microns. The sites can each have an area of less than 1 square millimeter, 500 square microns, 100 square microns, 25 square microns, 1 square micron or less. A site of an array may also be referred to herein as a 'feature' of the array.

Various publications, patents, and/or patent applications may have been referenced. The disclosures of these documents in their entireties are hereby incorporated by reference in this application.

It is noted that the embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc.

A number of embodiments have been described. Nevertheless, it will be understood that various modifications may be made. Accordingly, other embodiments are within the scope of the following claims.

What is claimed is:

1. A system for DNA sequencing, the system comprising:
a solid support configured for attachment of one or more analytes or reagents;
an objective lens having a depth of field equal to or less than 1.5 microns, the objective lens comprising:
a first doublet lens having a first lens and a second lens, wherein:
the first lens of the first doublet lens has a concave and a convex surface; and
the second lens of the first doublet lens has a concave and a convex surface;
a second doublet lens having a first lens and a second lens, wherein:
the first lens of the second doublet lens has a concave and a convex surface; and
the second lens of the second doublet lens has a concave and a convex surface;
a third doublet lens having a first lens and a second lens, wherein:
the first lens of the third doublet lens has two convex surfaces;
the second lens of the third doublet lens has two concave surfaces; and
the second doublet lens is between the first doublet lens and the third doublet lens;
a fourth doublet lens having a first lens and a second lens, wherein:
the first lens of the fourth doublet lens has two concave surfaces;
the second lens of the fourth doublet lens has two convex surfaces;
the third doublet lens is between the second doublet lens and the fourth doublet lens;
the first doublet lens is a first lens of an optical train of the objective lens and the fourth doublet lens is a last lens of the optical train of the objective lens;
the first doublet lens is configured to be closer to the solid support than the fourth doublet lens; and
optical rays are not infinity corrected after passing from the first doublet lens through the fourth doublet lens;
a first singlet lens between the second doublet lens and the third doublet lens, the first singlet lens having two convex surfaces;
a second singlet lens between the second doublet lens and the third doublet lens, the second singlet lens having two convex surfaces;
an aspheric lens between the third doublet lens and the fourth doublet lens, wherein the aspheric lens has a diameter equal to or greater than 40 millimeters and equal to or less than 60 millimeters; and
an aperture stop between the third doublet lens and the fourth doublet lens, wherein:
the aperture stop is a physical aperture stop having one or more walls forming an opening;
the aperture stop is within 25 millimeters of the aspheric lens; and
the aperture stop is located at a distance between 70% and 90% in the optical train measured from the first doublet lens;
a camera configured to image luminescence from analytes or reagents on the solid support using the objective lens;
a tube lens between the objective lens and the camera, the tube lens configured to focus light from the objective lens onto a sensor of the camera;
an excitation source; and
a dichroic mirror between the objective lens and the lens tube, the dichroic mirror configured to reflect light from the excitation source into the objective lens toward the solid support, wherein:
light from the excitation source is configured to cause material of the one or more analytes or reagents to fluoresce; and
the dichroic mirror is at an angle less than 40 degrees with respect to the aspheric lens.

2. The system of claim 1, wherein the objective lens has no more than 22 surfaces of lenses that affect optical power of the objective lens, 16 surfaces from four doublet lenses, four surfaces from two singlet lenses, and two surfaces from the aspheric lens.

3. The system of claim 1, wherein optical elements of the objective lens consist of four doublet lenses, two singlet lenses, the aspheric lens, and the aperture stop.

4. The system of claim 1, wherein:
the solid support is part of a flow cell;
the flow cell comprises a cover slip; and
the cover slip is 1 millimeter thick.

5. An apparatus for an objective lens of a microscope for imaging an array of nucleic acids, the apparatus comprising:
a plurality of lenses having simple surfaces, wherein:
the plurality of lenses form an optical train, the optical train extending from a first lens to a last lens; and
the plurality of lenses comprise four doublet lenses and no triplet lenses;
an aperture stop, wherein:
the aperture stop is a physical aperture stop; and
the aperture stop is located between the first lens and the last lens; and
an aspheric lens between the first lens and the last lens, the aspheric lens positioned within 10 millimeters of the aperture stop.

6. The apparatus of claim 5, wherein:
the first lens is configured to be closer to a specimen than the last lens; and the aperture stop is located at a distance between 70% and 90% in the optical train as measured from the first lens.

7. The apparatus of claim 5, wherein optical rays are not infinity corrected after passing through the last lens of the optical train.

8. The apparatus of claim 5, wherein the aspheric lens has a diameter equal to or greater than 40 millimeters and equal to or less than 60 millimeters.

9. The apparatus of claim 5, wherein the apparatus has a depth of field equal to or less than 1.5 microns.

10. The apparatus of claim 9, wherein the apparatus has a numerical aperture between 0.6 and 0.8.

11. The apparatus of claim 10, wherein the apparatus has a field of view that is at least 1 mm$^2$.

12. A system for DNA sequencing, the system comprising:
   a solid support configured for attachment of an array of nucleic acids;
   an objective lens comprising:
      a plurality of lenses having simple surfaces;
      an aperture stop, wherein the aperture stop is a physical aperture stop; and
      an aspheric lens positioned within 25 millimeters of the aperture stop, wherein the aspheric lens has a diameter equal to or greater than 40 millimeters and equal to or less than 60 millimeters; and
   a camera configured to image the array using the objective lens.

13. The system of claim 12, further comprising a mirror between the objective lens and the camera, wherein the mirror is at an angle less than 40 degrees with respect to the aspheric lens.

14. The system of claim 12, wherein the solid support is part of a flow cell, and the flow cell has a coverslip having a thickness equal to or greater than 0.3 millimeters and equal to or less than 2.0 millimeters.

15. The system of claim 12, wherein a first lens of the objective lens is separated by a distance from the solid support, and the distance is equal to or less than 10 millimeters and equal to or greater than 3 millimeters.

16. The system of claim 12, wherein:
   the plurality of lenses form an optical train, the optical train extending from a first lens to a last lens; and
   the plurality of lenses comprise four doublet lenses and no triplet lenses.

17. The system of claim 12, wherein the system has a depth of field equal to or less than 1.5 microns.

18. The system of claim 17, wherein the system has a numerical aperture between 0.6 and 0.8.

19. The system of claim 12, wherein the system has a field of view that is at least 4 mm$^2$.

20. The system of claim 12, further comprising the array of nucleic acids attached to the solid support.

* * * * *